United States Patent
Lejeune et al.

(10) Patent No.: US 10,294,251 B2
(45) Date of Patent: May 21, 2019

(54) PROCESS FOR PREPARING ALKOXYSILANES

(71) Applicant: Momentive Performance Materials Inc., Waterford, NY (US)

(72) Inventors: Alain Lejeune, Reignier (FR); Antonio Chaves, Chappaqua, NY (US); Tiberiu Simandan, Termoli (IT); Ilaria Vecchi, Casalbordino (IT); Lesley Hwang, Chappaqua, NY (US); Andrea Trotto, Termoli (IT)

(73) Assignee: Momentive Performance Materials Inc., Waterford, NY (US)

( * ) Notice: Subject to any disclaimer, the term of this patent is extended or adjusted under 35 U.S.C. 154(b) by 15 days.

(21) Appl. No.: 15/616,091

(22) Filed: Jun. 7, 2017

(65) Prior Publication Data

US 2017/0355720 A1   Dec. 14, 2017

Related U.S. Application Data

(60) Provisional application No. 62/348,436, filed on Jun. 10, 2016.

(51) Int. Cl.
*C07F 7/20* (2006.01)
*C07F 7/18* (2006.01)

(52) U.S. Cl.
CPC ............ *C07F 7/188* (2013.01); *C07F 7/1804* (2013.01); *C07F 7/20* (2013.01)

(58) Field of Classification Search
None
See application file for complete search history.

(56) References Cited

U.S. PATENT DOCUMENTS

| | | | |
|---|---|---|---|
| 2,820,806 A * | 1/1958 | Haslam | B01J 31/0212 502/171 |
| 6,005,132 A | 12/1999 | Weidner et al. | |
| 7,368,584 B2 | 5/2008 | Chaves et al. | |
| 7,504,456 B2 | 3/2009 | Chaves et al. | |
| 7,560,583 B2 | 7/2009 | Chaves et al. | |
| 7,718,819 B2 | 5/2010 | Chaves et al. | |
| 7,919,650 B2 | 4/2011 | Chaves et al. | |
| 8,008,519 B2 | 8/2011 | Chaves et al. | |
| 9,273,186 B2 | 3/2016 | Standke et al. | |

OTHER PUBLICATIONS

Kemmitt et al., J. Chem. Soc., Perkin Trans. 1, 1997, 729-739.*
Kemmitt et al., J. Chem. Soc. Perkin Trans. 1, 1997, 729-7239. (Year: 1997).*
Kemmitt et al., "Dendrimeric silatrane wedges"; J. Chem. Soc., Perkin Trans. 1, (1997) 729-739.
"Transesterification" from Wikipedia on Jun. 7, 2016.
Search Report and Written Opinion from PCT/US2017/036320 dated Sep. 6, 2017.

* cited by examiner

*Primary Examiner* — Clinton A Brooks
*Assistant Examiner* — Kofi Adzamli
(74) *Attorney, Agent, or Firm* — James C. Abruzzo

(57) ABSTRACT

A transesterification process for preparing alkoxysilane includes removal of metal transesterification catalyst from the alkoxysilane transesterification reaction medium.

20 Claims, No Drawings

PROCESS FOR PREPARING ALKOXYSILANES

CROSS REFERENCE TO RELATED APPLICATION

This application claims priority to provisional U.S. patent application Ser. No. 62/348,436, filed Jun. 10, 2016, the entire contents of which are incorporated by reference herein.

FIELD OF THE INVENTION

The present invention relates to a catalytic transesterification process for preparing alkoxysilanes.

BACKGROUND OF THE INVENTION

Alkoxysilanes may be prepared by transesterification of a transesterifiable alkoxysilane (reactant) with an alcohol in the presence of a metal transesterification catalyst to produce an alkoxysilane transesterification reaction product in which at least one alkoxy group of the transesterifiable alkoxysilane is exchanged with the alkoxy group of the esterifying alcohol. As the transesterification reaction proceeds, the byproduct alcohol produced in the transesterification reaction is removed often from the reaction medium to drive the reaction to completion. In the aforedescribed transesterification process, the transesterification catalyst may be separated from the alkoxysilane transesterification reaction product by distillation, or the catalyst may remain in the alkoxysilane transesterification reaction product. Indeed, for some uses, the metal transesterification catalyst presence in the alkoxysilane reaction product may be desirable.

In the aforedescribed process for preparing alkoxysilanes transesterification reaction products, the metal transesterification catalyst, which may be present in the alkoxysilane reaction product, may cause siloxane formation, especially over normal or expected periods of storage, for example, from 1 month to 4 years duration. The siloxanes formation can negatively impact product purity, even to the extent of rendering the product unacceptable for use.

In some cases, retained metal transesterification catalyst may precipitate out of solution thereby interfering with subsequent handling, for example, pumping from storage in the course of a downstream manufacturing operation.

The metal transesterification catalyst may have a boiling point similar to the alkoxysilane reaction product or form an azeotrope with said product. Under these circumstances, the catalyst and product may co-distill and therefore would not effectively remove the metal transesterification catalyst from the alkoxysilane transesterification reaction product. The co-distillation of the catalyst and alkoxysilane transesterification reaction product following completion of the transesterification reaction may also interfere with proper operation of the condenser, specifically, by the accumulation of solids therein. And, as noted above, catalyst present in the alkoxysilane transesterification reaction product may cause siloxane formation or precipitate out of solution.

It will also be noted that metal transesterification catalyst present in the alkoxysilane transesterification reaction product may cause unwanted chemical reaction(s) to occur or accelerate hydrolysis and condensation reaction product of the alkoxysilane transesterification reaction product. These reactions depend on the nature of the alkoxysilane transesterification reaction product and the particular use to which the product is put, as for example, the reaction of epoxides with amines, siloxane formation or crosslinking of silylated polymers, which can reduce the shelf life of an end use product.

A need therefore exists for a process to remove part or substantially all of the metal transesterification catalyst from the alkoxysilane transesterification reaction product, thereby eliminating any interference with the proper operation of condensers during distillation or other separation processes.

SUMMARY OF THE INVENTION

In accordance with the present invention, there is provided a process for preparing an alkoxysilane transesterification reaction product which comprises the transesterification of at least one transesterifiable alkoxysilane with at least one alcohol in the presence of at least one metal transesterification catalyst under transesterification reaction conditions, optionally accompanied by removal of byproduct alcohol and/or unreacted alcohol, to produce an alkoxysilane transesterification reaction product followed by removal of at least part of the catalyst from the reaction product.

The removal of the metal transesterification catalyst from the alkoxysilane transesterification reaction product is achieved by either (i) subjecting catalyst to hydrolysis to form metal oxide precipitates, and then followed by filtration to remove the metal oxide precipitates, or (ii) adsorption of the metal transesterification catalysts onto a suitable absorption media.

In accordance with the present invention, by removing at least a significant part of the metal transesterification catalyst that remains in the alkoxysilane transesterification reaction product after completion of the transesterification, the aforementioned problems of gelling, catalyst precipitation, condenser malfunction and unwanted chemical reaction(s) are mitigated, or with the substantially complete separation of catalyst from the reaction product, for example, at least about 80 percent, preferably at least about 90 percent, and more preferably at least about 95 percent by weight separation of catalyst from the reaction product, largely or even totally eliminated.

DETAILED DESCRIPTION OF THE INVENTION

In the specification and claims herein, the following terms and expressions are to be understood as indicated.

The singular forms "a," "an," and "the" include the plural, and reference to a particular numerical value includes at least that particular value, unless the context clearly dictates otherwise.

The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

The terms, "comprising," "including," "containing," "characterized by," and grammatical equivalents thereof are inclusive or open-ended terms that do not exclude additional, unrecited elements or method steps, but will also be understood to include the more restrictive terms "consisting of" and "consisting essentially of."

All numerical values shall be understood herein to be modified by the term "about" except in the case of the working examples or where a particular value is expressly indicated to be exact.

It will be understood that any numerical range recited herein includes all sub-ranges within that range and any combination of the various endpoints of such ranges or sub-ranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

The term "alkyl" means any monovalent, saturated straight or branched hydrocarbon group; the term "alkenyl" means any monovalent straight or branched hydrocarbon group containing one or more carbon-carbon double bonds where the site of attachment of the group can be either at a carbon-carbon double bond or elsewhere therein; and, the term "alkynyl" means any monovalent straight or branched hydrocarbon group containing one or more carbon-carbon triple bonds and, optionally, one or more carbon-carbon double bonds, where the site of attachment of the group can be either at a carbon-carbon triple bond, a carbon-carbon double bond or elsewhere therein. Examples of alkyls include methyl, ethyl, propyl and isobutyl. Examples of alkenyls include vinyl, propenyl, allyl or methallyl. Examples of alkynyls include acetylenyl, propargyl and methylacetylenyl.

The term "cycloalkyl" means any monovalent hydrocarbon group containing a ring structure; the term "cycloalkenyl" means any monovalent hydrocarbon group containing a ring structure and one or more carbon-carbon double bonds where the site of attachment of the group can be either at a carbon-carbon double bond or elsewhere therein; and, the term "cycloalkynyl" means any monovalent hydrocarbon group containing a ring structure and one or more carbon-carbon triple bonds and, optionally, one or more carbon-carbon double bonds, where the site of attachment of the group can be either at a carbon-carbon triple bond, a carbon-carbon double bond or elsewhere therein. The expressions "cycloalkyl", "cycloalkenyl", and "cycloalkynyl" include monocyclic, bicyclic, tricyclic and higher cyclic structures as well as the aforementioned cyclic structures further substituted with alkyl, alkenyl, and/or alkynyl groups. Representative examples include norbornyl, norbornenyl, ethylnorbornyl, ethylnorbornenyl, cyclohexyl, ethylcyclohexyl, ethylcyclohexenyl, cyclohexylcyclohexyl, cyclododecatrienyl, ethylidene norbornyl, ethylidenyl norbornene and ethylidene norbornenyl.

The term "aryl" means any monovalent aromatic hydrocarbon group; the term "aralkyl" means any alkyl group (as defined herein) in which one or more hydrogen atoms have been substituted by the same number of like and/or different aryl (as defined herein) groups; and, the term "arenyl" means any aryl group (as defined herein) in which one or more hydrogen atoms have been substituted by the same number of like and/or different alkyl groups (as defined herein). Examples of aryls include phenyl and naphthalenyl. Examples of aralkyls include benzyl and phenethyl. Examples of arenyls include tolyl and xylyl.

The expression "transesterification reaction medium" shall be understood herein to include such a medium when formed, as existing at any particular moment during transesterification and as existing following completion of transesterification.

The expression "alkoxysilane transesterification reaction product" as used herein shall be understood to include monomeric, dimeric or oligomeric alkoxysilane transesterification reaction products and in the case of dimeric and oligomeric alkoxysilane transesterification reaction products, possessing dialkoxy bridging groups linking adjacent silane units.

In one embodiment of the present invention, alkoxysilane transesterification reaction products and their mixtures can be obtained from the reaction of one or more transesterifiable alkoxysilanes of general formula (I):

$$Y-[R^1-Si(R^2)_{3-a}(OR^3)_a]_b \qquad (I)$$

wherein:

Y is hydrogen, halo or a functional group;

each $R^1$ independently is a divalent straight chain alkylene group of from 1 to 12 carbon atoms, a branched chain alkylene of from 2 to 12 carbon atoms, a cycloalkylene group of from 3 to 12 carbon atoms, an arylene group of from 6 to 10 carbon atoms, an aralkyl group of from 7 to 16 carbon atoms, an alkenylene group of from 2 to 12 carbon atoms, a cycloalkenylene group of from 3 to 12 carbon atoms, an alkynylene group of from 2 to 12 carbon atoms, a straight alkylene, branched alkylene or cycloalkylene group containing at least one heteroatom chosen from sulfur, oxygen or nitrogen and from 2 to 12 carbon atoms, or a chemical bond, with the proviso that where $R^1$ is a chemical bond, Y is an organofunctional group, the silicon atom being bonded to a carbon atom of group Y;

each $R^2$ independently is a monovalent straight chain alkyl group containing 1 to 16 carbon atoms, a branched alkyl group containing 3 to 16 carbon atoms, a cycloalkyl group containing 3 to 12 carbon atoms, an aryl group containing 6 to 10 carbon atoms, an aralkyl group containing 7 to 16 carbon atoms;

each $R^3$ independently is a monovalent straight chain alkyl group of from 1 to 4 carbon atoms or a branched chain alkyl group having 3 to 4 carbon atoms;

a is an integer of from 1 to 3; and, b is an integer of from 1 to 4, under catalytic transesterification reaction conditions, with one or more transesterifying alcohols of general formula (II):

$$R^4OH \qquad (II)$$

wherein:

$R^4$ is a monovalent straight chain alkyl group of from 1 to 16 carbon atoms, a branched chain alkyl group of from 3 to 16 carbon atoms, a cycloalkyl group of from 3 to 12 carbon atoms, an alkenyl group of from 2 to 16 carbon atoms, an aralkyl group of from 7 to 12 carbon atoms, an aryl group of from 6 to 10 carbon atoms, a straight chain alkyl group containing at least one heteroatom selected from oxygen, sulfur or nitrogen containing from 2 to 16 carbon atoms or a branched alkyl group containing at least one heteroatom selected from oxygen, sulfur or nitrogen containing from 3 to 16 carbon atoms, a straight or branched alkyl group of from 2 to 16 carbon atoms and substituted with at least on hydroxyl or amino group, —$NR^5R^6$ where $R^5$ and $R^6$ are independently hydrogen or a straight chain alkyl group of from 1 to 16 carbon atoms, a branched chain alkyl group of from 3 to 16 carbon atoms, an aryl group of from 6 to 10 carbon atoms or an aralkyl group of from 7 to 12 carbon atoms, in the presence of a catalytically effective amount of one or more metal transesterification catalysts of general formula (III):

$$M^{n+}(X)_n \qquad (III)$$

wherein:

M is a metal that is catalytically active for transesterification;

X is $OR^7$ where each $R^7$ is independently a monovalent straight chain alkyl group of from 1 to 12 carbon atoms, a branched chain alkyl group of 3 to 12 carbon atoms, a cycloalkyl group of from 3 to 12 carbon atoms, an aryl group of from 6 to 10 carbon atoms, an aralyl group of from 9 to 12 carbon atoms, an alkenyl group of 2 to 12 carbon atoms, an acyl group of from 1 to 12 carbon atoms, or two $OR^7$ groups are bonded to each other through a carbon-carbon linkage to form a —O—$R^7$—$R^7$—O— group, or X is $R^8$ where $R^8$ is a monovalent straight chain alkyl group of from 1 to 16 carbon atoms, a branched chain alkyl group of from 3 to 16 carbon atoms, a cycloalkyl group of from 3 to 12 carbon atoms, an aryl group of from 6 to 10 carbon atoms or an aralkyl group of from 7 to 12 carbon atoms, with the proviso that at least one X is $OR^7$; and, n is the valence of M, optionally, accompanied by continuous removal of by-product and/or unreacted alcohol.

In transesterifiable alkoxysilane (I), each alkoxy group $OR^3$ independently is preferably methoxy, ethoxy, propoxy, isopropoxy, n-butoxy, sec-butoxy or tert-butoxy and more preferably is methoxy, ethoxy or propoxy, a is preferably 2 or 3 and more preferably 3, b is preferably 1 and Y is preferably hydrogen, halo, mercapto, glycidoxy, epoxycyclohexyl, ureido, carbamato, acryloxy, methacryloxy, amino or vinyl.

Specific transesterifiable alkoxysilanes (I) that can be made to undergo transesterification herein include but are not limited to methyltrimethoxysilane, methyltriethoxysilane, methyltripropoxysilane, propyltrimethoxysilane, propyltriethoxysilane, propyltripropoxysilane, butyltrimetoxysilane, butyltriethoxysilane, butyltripopoxysilane, hexyltrimethoxysilane, hexyltriethoxysilane, hexyltripropoxysilane, octyltrimethoxysilane, octyltriethoxysilane, octyltripropoxysilane, 3-chloropropyltrimethoxysilane, 3-chloropropyltriethoxysilane, 3-chloropropyltripropoxysilane, 3-mercaptopropyltrimethoxysilane, 3-mercaptopropyltriethoxysilane, 3-mercaptopropyltripropoxysilane, 3-glycidoxypropyltrimethoxysilane, 3-glycidoxypropyltriethoxysilane, 3-glycidoxypropyltripropoxysilane, 3-ureidopropyltrimethoxysilane, 3-ureidopropyltriethoxysilane, 3-ureidopropyltripropoxysilane, (3,4-epoxycyclohexyl)ethyltrimethoxysilane, (3,4-epoxycyclohexyl)ethyltriethoxysilane, (3,4-epoxycyclohexyl)ethyltripropoxysilane, vinyltrimethoxysilane, vinyltriethoxysilane, vinyltripropoxysilane, propylmethyldimethoxysilane, propyldimethylmethoxysilane, octylmethyldimethoxysilane, octyldimethylmethoxysilane, 3-chloropropylmethyldimethoxysilane, 3-chloropropyldimethylmethoxysilane, 3-mercaptopropylmethyldimethoxysilane, 3-mercaptopropyldimethylmethoxysilane, 3-glycidoxypropylmethyldimethoxysilane, 3-glycidoxypropyldimethylmethoxysilane, 3-ureidopropylmethyldimethoxysilane, 3-ureidopropyldimethylmethoxysilane, (3,4-epoxycyclohexyl)ethylmethyldimethoxysilane, (3,4-epoxycyclohexyl)ethyldimethylmethoxysilane, vinylmethyldimethoxysilane and vinyldimethylmethoxysilane.

In transesterifying alcohol (II), $R^4$ is preferably a monovalent straight or branched alkyl. Thus, for example, where an $OR^3$ group in transestifiable alkoxysilane (I) is methoxy, $R^4$ of alcohol (II) is preferably ethyl or an alkyl of higher carbon number, where an $OR^3$ is ethoxy, $R^4$ of alcohol (II) is preferably propyl, isopropyl or alkyl of higher carbon number, and so forth.

Specific transesterifying alcohols (II) that can be used to transesterify alkoxysilanes (I) to provide alkoxysilane transestification reaction products in accordance with the process of the invention include but are not limited to methanol, ethanol, propanol, butanol, isobutanol, pentanol, isopentanol, hexanol, isohexanol, and the like.

In metal transesterification catalyst (III), M is preferably Ti, Zr, Bi, Zn, Sn or mixtures thereof and each X is preferably $OR^7$ where $R^7$ is a straight or branched alkyl group of from 1 to 6 carbon atoms or an acyl group of from 1 to 6 carbon atoms.

Specific metal transesterification catalysts (III) that can be used herein to catalyze the transesterification reaction include but are not limited to alkyl titanates such as methyl-, ethyl-, propyl-, isopropyl-, butyl-, sec-butyl-, tert-butyl- and 2-ethylhexyltitanates, alkyl zirconates such as ethyl-, propyl- and butyl zirconates, alkyl bismuthates such as bismuth (2-ethylhexanoate), bismuth neodecanoate and bismuth tetramethylheptanedioate and alkyl stannates such as dibutyltin dilaurate, dioctyltin dineodecanoate and dimethyltin dioleate.

Metal transesterification catalyst (III) will be present in the transesterification reaction medium in at least a catalytically effective amount. The amounts of catalyst can vary widely, for example, in one embodiment from about 0.01 weight percent to about 5 weight percent, in another embodiment from about 0.1 weight percent to about 3 weight percent and in yet another embodiment from about 0.5 weight percent to about 2 weight percent, based on the total weight of transesterifiable alkoxysilane (I).

Catalytic transesterification reaction conditions include those known by those of ordinary skill in the art and may vary widely depending on the nature and amount of transesterifiable alkoxysilane (I), transesterifying alcohol (II), metal transesterification catalyst (III) and catalyst concentration. In general and as well known in the art, the transesterification reaction will be carried out within a range of temperature and pressure whereby byproduct and/or unreacted alcohol may be recovered as the reaction proceeds. Ordinarily, the reaction will be carried out substantially to completion, for example, up to about 80 weight percent, and preferably up to about 90 weight percent or greater, based upon the original amount of the transesterifiable alkoxysilane (I), where the extent of completion as determined by known and conventional analytical techniques such as gas chromatography and NMR.

Reaction temperature is advantageously maintained below the boiling point of transesterifying alcohol (II) at the selected pressure of the transesterification reaction. A fractionating column may be used to aid in the removal of the byproduct alcohol. The byproduct is removed from the reaction medium during transesterification in order to drive the reaction to completion. Typical transesterification reaction conditions include temperatures from room temperature to about 120° C., more preferably from about 50° C. to about 100° C. and pressures ranging from about 0.0007 bar to about 2 bar, more preferably from about 0.02 bar to about 1 bar.

Following transesterification reaction, the metal transesterification catalyst (III) is removed either to a partial or an essentially complete extent. In an embodiment, techniques of removal include subjecting the catalyst to hydrolysis followed by filtration to remove metal oxide precipitate resulting from the hydrolysis reaction, or adsorption of the catalyst on suitable absorption media. In general, such techniques and their combinations will be used to remove at least a significant amount of metal transesterification catalyst from the final alkoxysilane transesterification reaction product, for example, reducing the amount of residual metal transesterification catalyst to less than about 100 ppm, preferably less than about 50 ppm, and more preferably less than about 10 ppm based on the weight of the alkoxysilane transesterification reaction product.

In the case of hydrolysis as the catalyst removal technique, sufficient water is added at room temperature to completely hydrolyze the metal catalyst. In one embodiment, the amount of water typically used is from about 0.1 to about 10 weight percent and preferably from about 1 to about 5 weight percent, based on the weight of the alkoxysilane transesterification reaction product. The reaction mixture containing hydrolyzed metal catalyst is filtered. The filtration can be aided by using typical filtration aids such as, for example, diatomaceous earth. Filtration removes metal oxide and much or all of the water used for the hydrolysis of the catalyst. The alkoxysilane may then be subjected to distillation to further purify the product, for example, to remove residual water and/or byproduct and/or unreacted alcohol.

In one embodiment, the hydrolysis conditions to convert the metal transesterification catalyst (III) to a metal oxide are a temperature of from about 1° C. to about 75° C. and preferably from about 15° C. to about 30° C., and a pressure of from about 0.0007 bar to about 2 bar and preferably from about 0.5 bar to about 1.2 bar.

In one embodiment, the alkoxysilane transesterification reaction product has the general formula (IV):

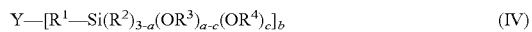

$$Y-[R^1-Si(R^2)_{3-a}(OR^3)_{a-c}(OR^4)_c]_b \qquad (IV)$$

wherein:

Y is hydrogen, halo or a functional group;

each $R^1$ independently is a divalent straight chain alkylene group of from 1 to 12 carbon atoms, a branched chain alkylene of from 2 to 12 carbon atoms, a cycloalkylene group of from 3 to 12 carbon atoms, an arylene group of from 6 to 10 carbon atoms, an aralkyl group of from 7 to 16 carbon atoms, an alkenylene group of from 2 to 12 carbon atoms, a cycloalkenylene group of from 3 to 12 carbon atoms, an alkynylene group of from 2 to 12 carbon atoms, a straight alkylene, branched alkylene or cycloalkylene group containing at least one heteroatom chosen from sulfur, oxygen or nitrogen and from 2 to 12 carbon atoms, or a chemical bond, with the proviso that where $R^1$ is a chemical bond, Y is an organofunctional group, the silicon atom being bonded to a carbon atom of group Y;

each $R^2$ independently is a monovalent straight chain alkyl group containing 1 to 16 carbon atoms, a branched alkyl group containing 3 to 16 carbon atoms, a cycloalkyl group containing 3 to 12 carbon atoms, an aryl group containing 6 to 10 carbon atoms, an aralkyl group containing 7 to 16 carbon atoms;

each $R^3$ independently is a monovalent straight chain alkyl group of from 1 to 4 carbon atoms or a branched chain alkyl group having 3 to 4 carbon atoms;

each $R^4$ is a monovalent straight chain alkyl group of from 1 to 16 carbon atoms, a branched chain alkyl group of from 3 to 16 carbon atoms, a cycloalkyl group of from 3 to 12 carbon atoms, an alkenyl group of from 2 to 16 carbon atoms, an aralkyl group of from 7 to 12 carbon atoms, an aryl group of from 6 to 10 carbon atoms, a straight chain alkyl group containing at least one heteroatom selected from oxygen, sulfur or nitrogen containing from 2 to 16 carbon atoms or a branched alkyl group containing at least one heteroatom selected from oxygen, sulfur or nitrogen containing from 3 to 16 carbon atoms, a straight or branched alkyl group of from 2 to 16 carbon atoms and substituted with at least on hydroxyl or amino group, $NR^5R^6$ where $R^5$ and $R^6$ are independently hydrogen or a straight chain alkyl group of from 1 to 16 carbon atoms, a branched chain alkyl group of from 3 to 16 carbon atoms, an aryl group of from 6 to 10 carbon atoms or an aralkyl group of from 7 to 12 carbon atoms a is an integer of from 1 to 3;

b is an integer of from 1 to 4; and c is an integer of from 1 to 3;

with the provisos that a and b are the value chosen for the transesterifiable alkoxysilane (I) and c is chosen so that a-c is 0 or a positive integer.

In one embodiment, in alkoxysilane transesterification reaction product (IV), a=3, b=0 and c=3.

If desired, in an embodiment the alkoxysilanes transesterification reaction product may be blended with a small amount of an acid such as acetic acid or boric acid as an aid to its hydrolysis and condensation at the time of use. In an embodiment, the amount of acid used may be from about 1 ppm to about 2 weight percent, more preferably from about 50 ppm to about 500 ppm, based on the total weight of the alkoxysilane transesterification reaction product.

In the case of adsorption as the catalyst removal technique, a solid is used as an adsorption medium, such as fumed or precipitated silica, clays, ion exchange resin or other particulate minerals, where the adsorption medium may be added to adsorb the metal catalyst. When the transesterification is complete, the absorption media, e.g., precipitated silica, is added to the reaction mixture and stirred. This is followed by filtration to remove the absorption media containing the metal catalyst.

In one embodiment, the process for preparing the alkoxysilane transesterification reaction product comprises:

(a) combining metal transesterification catalyst, for example, in an amount of from about 0.005 to about 5 weight percent, preferably from about 0.01 to about 1 weight percent, based on the weight of transesterifiable alkoxysilane, to a transesterifiable alkoxysilane to provide a mixture thereof;

(b) subjecting the mixture from step (a) to esterification reaction conditions upon addition of transesterifying alcohol thereto, for example, a temperature of from ambient to about 120° C. and a pressure of from about 0.0007 bar to about 2 bar, preferably from about 0.02 bar to about 1 bar;

(c) adding transesterifying alcohol to the mixture of metal transesterification catalyst and transesterificable alkoxysilane prior to and/or during step (b) to provide a transesterification reaction medium thereby commencing transesterification and producing alkoxysilane transesterification reaction product;

(d) removing byproduct alcohol formed during transesterification from the transesterification reaction medium;

(e) separating metal transesterification catalyst from the transesterification reaction medium of step (d) to provide a catalyst-depleted transesterification reaction medium containing alkoxysilane transesterification reaction product, such separating being accomplished by, for example, (i) hydrolyzing metal transesterification catalyst under hydrolysis-effective conditions such as a temperature of from about 1° C. to about 75° C., preferably from about 15° C. to about 40° C., a pressure of from about 0.01 bar to about 2 bar, preferably from about 0.5 bar to about 1.2 bar, and an amount of water of from about 0.1 to about 10 weight percent, preferably from about 0.2 to about 8 weight percent, based on the weight of alkoxysilane transesterification product, to provide metal oxide-containing hydrolyzate which is thereafter removed from the transesterification reaction medium, for example, by filtration or decantation, or (ii) adsorbing metal transesterification catalyst on an adsorption medium, transesterification catalyst-containing adsorption medium thereafter being removed from the transesterification reaction medium, for example, by filtration or decantation; and, optionally, (f) separating alkoxysilane transesterification reaction product from the transesterification catalyst-depleted transesterification reaction medium of step (e) such as by distillation.

The following examples are illustrative of the process of the invention.

Example 1

Preparation of 3-Glycidoxypropyltriethoxysilane

This example illustrates the production of 3-glycidyloxypropyltriethoxysilane transesterification reaction product employing titanium isopropoxide (TPT) as metal-containing transesterification catalyst.

A 5-liter flask equipped with a mechanical stirrer, a heating mantle, a temperature probe connected to a temperature controller, a short path distillation head and maintained under a nitrogen blanket was charged with 3-glycidyloxypropyltrimethoxysilane (2587.0 grams, 10.95 moles) and TPT catalyst (31.5 grams, 0.11 mole). The mixture was stirred at 290 rpm, the temperature set at 100° C. and the pressure at about 1 bar. Once at temperature, ethanol addition (6783.4 grams, 147.25 moles) was started. The ethanol was added to the reactor over about 12 hours through a piston pump, the feed rate being adjusted to the desired value. During the addition of ethanol, byproduct methanol and excess ethanol were removed using a short path distillation procedure. The amount of crude product formed was 3295.0 grams and the amount of titanium was 1611 ppm.

After the transesterification reaction reached the desired conversion, the crude reaction mixture was allowed to cool to ambient temperature. Then, about 5 weight percent of demineralized water was added to the crude 3-glycidyloxypropyltriethoxysilane and stirred for 1.5 to 2 hours. Immediately after the water addition, the appearance of the crude reaction mixture turned from a yellow clear liquid into a white hazy solution due to the hydrolysis of TPT and the precipitation of the titanium oxide hydrolyzate.

About 1 weight percent of a filter aid, diatomaceous earth, was added to the reactor before filtration. After filtration through a 1 μm pore size PTFE membrane (5 bar pressure), the appearance of the crude product was slightly yellow and clear.

The crude product was then distilled in a batch distillation. The material was charged to a 5-liter round-bottomed flask equipped with a heating mantle, a temperature probe connected to a temperature controller, magnetic stirrer and a stirrer bar, a short path distillation head with multiple receivers and a cold trap. The distillation conditions were: 6 mmHg and 138° C. overhead. The lights were mainly water and ethanol while the heavies were mainly siloxanes and 213 ppm Ti. The appearance of the distilled material was slightly yellow and clear. The purity by GC was 97.0 percent and the amount of titanium metal was less than 10 ppm titanium. These data, along with the charges and crude product before hydrolysis, are presented in Table 1.

Example 2

Preparation of 3-Glycidoxypropyltriethoxysilane

This example was carried out under conditions similar to those of Example 1 except that the charges were slightly different. The amount of glycidoxypropyltrimethoxysilane was 3512.5 grams, TPT was 40.0 grams and ethanol was 9500.8 grams. The amount of crude product formed was 4496.9 grams and the amount of titanium was 1499 ppm.

Purity as determined by GC was 97.2 percent with less than 10 ppm titanium. These data, with the charges and crude product before hydrolysis, are presented in Table 1 below.

Example 3

Removal of TPT from 3-Glycidoxypropyltriethoxysilane Transesterification Reaction Medium by Hydrolysis and Filtration This example demonstrates the effectiveness of hydrolysis and filtration for the removal of TPT from the transesterification reaction medium and subsequent distillation for the recovery of 3-glycidoxypropyltriethoxysilane reaction product from the TPT-depleted reaction medium.

A 0.5-liter flask equipped with a mechanical stirrer, a heating mantle, a temperature probe connected to a temperature controller, a short path distillation head and under a nitrogen blanket was charged with 3-glycidyloxypropyltrimethoxysilane (264.9 grams, 1.12 moles) and TPT (3.2 grams, 0.01 mol). The mixture was stirred at 290 RPM and the temperature was set at 100° C. and about 1 bar. Once at temperature, the ethanol (577.8 grams, 12.5 moles) addition was started. The ethanol was added to the reactor through a piston pump and the feed rate was adjusted just before the experiment to the desired value. The ethanol addition took about 11 hours. During the addition of ethanol, the byproduct methanol and excess ethanol were removed using a short path distillation process. The amount of crude product formed was 338.10 grams and the amount of titanium was 2445 ppm.

Once the reaction reached the desired conversion, the crude reaction mixture was allowed to cool to ambient temperature. Then, about 2 weight percent of demineralized water was added to the crude 3-glycidyloxypropyltriethoxysilane and kept under stirring for 1.5 to 2 hours. Immediately after the water addition, the appearance of the crude reaction mixture turned from a yellow clear liquid to a white hazy solution due to the hydrolysis of TPT and precipitation of the titanium oxide. About 1% of filter aid was added to the reactor before filtration. After filtration through a 1 μm pore size PTFE membrane (5 bar pressure), the appearance of the crude reaction product was slightly yellow and clear.

The crude reaction product was then distilled in a batch distillation. The material was charged to a 0.5 liter round-bottomed flask equipped with a heating mantle, a temperature probe connected to a temperature controller, magnetic stirrer and a stirrer bar, a short path distillation head with multiple receivers and a cold trap. The distillation conditions were: 6 mmHg and 138° C. overhead. The lights were mainly water and ethanol, while the heavies were mainly siloxanes and 213 ppm Ti. The appearance of the distilled material was slightly yellow and clear. The purity by GC was 95.9 percent and the amount of titanium metal was less than 3.5 ppm titanium. These data, along with the charges and crude product before hydrolysis, are presented in Table 1.

Comparison Example 1

Preparation and Recovery of
3-Glycidoxypropyltriethoxysilane Without Prior Removal of TPT This comparison example shows that TPT will contaminate distilled 3-glycidyloxypropyltriethoxysilane transesterification reaction product unless at least a substantial amount, for example, at least 90, preferably at least 95 and more preferably at least 99, weight percent of the TPT is removed prior to recovery of the reaction product from the transesterification reaction medium.

A 1-liter flask equipped with a mechanical stirrer, heating mantle, temperature probe connected to a temperature controller, short path distillation head and source of nitrogen was charged with 3-glycidyloxypropyltrimethoxysilane (300.2 grams, 1.27 moles) and TPT (3.7 grams, 0.013 mole). The mixture was stirred at 290 rpm, the temperature set at 100° C. and the pressure at about 1 bar. Once at temperature, ethanol (552.3 grams, 12.0 moles) addition was started. The ethanol was added to the reactor through a piston pump and the feed rate was adjusted just before the run to the desired value. Ethanol addition took about 11 hours. The amount of crude product formed was 339.8 grams and the amount of titanium was 2049 ppm.

The crude reaction product was then distilled in a batch distillation. The material was charged to a 1-liter round-bottomed flask equipped with a heating mantle, a temperature probe connected to a temperature controller, magnetic stirrer and stirrer bar, a 10-plate Oldershaw distillation column, a variable reflux distillation head with multiple receivers and a cold trap. The distillation conditions for were: 6 mmHg and 138° C. overhead. The lights were mainly methanol and ethanol while the heavies were mainly siloxane. The distilled material was a clear liquid with dispersed white solids. TPT co-distilled with the 3-glycidyloxypropyltriethoxysilane and use of a 10 plate column and a reflux ratio of about 10 failed to separate these two materials. As a result, TPT heavily contaminated the distilled 3-glycidyloxypropyltriethoxysilane. The TPT (melting point=15-17° C.) crystallized upon cooling in the distillation head which in turn caused plugging within the unit.

Table 1 below sets forth the charges of reactants, catalyst and compositions of the transesterification reaction product before and after catalyst removal and distillation for Examples 1-3 and Comparison Example 1:

TABLE 1

|  | Example 1 | Example 2 | Example 3 | Comparison Example 1 |
| --- | --- | --- | --- | --- |
| Reactants, Catalyst |  |  |  |  |
| 3-Glycidoxypropyltrimethoxysilane, grams | 2587.0 | 3512.5 | 264.9 | 300.2 |
| Ethanol, grams | 6783.4 | 9500.8 | 577.8 | 552.3 |
| TPT, grams | 31.5 | 40.0 | 3.2 | 3.7 |
| Product, crude, before hydrolysis to remove TPT |  |  |  |  |
| 3-Glycidoxypropyltriethoxysilane, grams | 3295.0 | 4496.9 | 338.1 | 339.8 |
| Ti, ppm | 1611 | 1499 | 2445 | 2049 |
| Product, final |  |  |  |  |
| 3-Glycidoxypropyltriethoxysilane, purity (wt %) | 97.0 | 97.2 | 95.9 | 94.6* |
| Ti, ppm (determined by ICP) | <10 | <10 | 3.5 | 545* |

*This value is relative only to the liquid phase. White solids that were present in the sample were not included.

Example 4

Removal of TPT from
3-Glycidoxypropyltriethoxysilane Transesterification Reaction Medium By Adsorption This example illustrates an adsorption procedure for removing metal transesterification catalyst from a 3-glycidyloxypropytriethoxysilane-containing transesterification reaction medium.

A 0.5-liter flask equipped with a mechanical stirrer, heating mantle, temperature probe connected to a temperature controller, short path distillation head and a source of nitrogen was charged with 3-glycidyloxypropyltrimethoxysilane and TPT. The mixture was stirred and the temperature was set at 100° C. Once at temperature, ethanol addition was started. The ethanol was added to the reactor over about 12 hours through a piston pump and the feed rate was adjusted to the desired value. The amounts of reactants were similar to those of Example 3.

After the reaction reached the desired conversion, 8 grams of precipitated silica was added to the crude reaction mixture and stirred at 100° C. for 1 hour. The reaction mixture was then cooled and filtered to remove the solids. The resulting product, 3-glycidyloxypropyltriethoxysilane, contained less than 100 ppm Ti as measured by ICP.

While the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention but that the invention will include all embodiments falling within the scope of the appended claims.

The invention claimed is:

1. A process for preparing an alkoxysilane transesterification reaction product which comprises
   (a) transesterifying at least one transesterifiable alkoxysilane with at least one transesterifying alcohol under transesterification reaction conditions in the presence of at least one metal transesterification catalyst accompanied by removal of byproduct and/or unreacted alcohol to produce a crude alkoxysilane transesterification reaction product; and
   (b) removing at least part of the metal transesterification catalyst from the reaction product, wherein removal of at least part of the metal transesterification catalyst from the reaction product of step (a) comprises hydrolyzing the metal transesterification catalyst to form a catalyst metal oxide and removing the catalyst metal oxide from the reaction product of step (a).

2. The process of claim 1 wherein the transesterifiable alkoxysilane is a transesterifiable alkoxysilane of general formula (I):

$$Y\text{---}[R^1\text{---}Si(R^2)_{3-a}(OR^3)_a]_b \quad (I)$$

wherein:
Y is hydrogen, halo or a functional group;
each $R^1$ independently is a divalent straight chain alkylene group of from 1 to 12 carbon atoms, a branched chain alkylene of from 2 to 12 carbon atoms, a cycloalkylene group of from 3 to 12 carbon atoms, an arylene group of from 6 to 10 carbon atoms, an aralkylene group of from 7 to 16 carbon atoms, an alkynylene group of from 2 to 12 carbon atoms, a straight, branched alkylene or cycloalkylene group containing at least one heteroatom selected from sulfur, oxygen or nitrogen and from 2 to 12 carbon atoms, or a chemical bond, with the proviso that when $R^1$ is a chemical bond, then Y is an organofunctional group and the silicon atom is bonded to a carbon atom of group Y;
each $R^2$ independently is a monovalent straight chain alkyl group containing 1 to 16 carbon atoms, a branched alkyl group containing 3 to 16 carbon atoms, a cycloalkyl group containing 3 to 12 carbon atoms, an aryl group containing 6 to 10 carbon atoms or an aralkyl group containing 7 to 16 carbon atoms;
each $R^3$ independently is a monovalent straight chain alkyl group of from 1 to 4 carbon atoms or a branched chain alkyl group having 3 to 4 carbon atoms;
a is an integer of from 1 to 3; and,
b is an integer of from 1 to 4.

3. The process of claim 2 wherein transesterifiable alkoxysilane (I) is at least one member selected from the group consisting of glycidoxypropyltrimethoxysilane, glycidoxypropyltriethoxysilane, (3,4-epoxycyclohexyl)ethyl trimethoxysilane and (3,4-epoxycyclohexyl)ethyl triethoxysilane.

4. The process of claim 2 wherein transesterifying alcohol is at least one member selected from the group consisting of ethanol, propanol, isopropanol and butanol.

5. The process of claim 2 wherein metal transesterification catalyst is at least one member selected from the group consisting of tetraisopropyl titanate, tetraethyl titanate, tetraethyl zirconate and tetrapropyl zirconate.

6. The process of claim 1 wherein the transesterifying alcohol is of general formula (II):

$$R^4OH \quad (II)$$

wherein:
$R^4$ is a monovalent straight chain alkyl group of from 1 to 16 carbon atoms, a branched chain alkyl group of from 3 to 16 carbon atoms, a cycloalkyl group of from 3 to 12 carbon atoms, an alkenyl group of from 2 to 16 carbon atoms, an aralkyl group of from 7 to 12 carbon atoms, an aryl group of from 6 to 10 carbon atoms, a straight chain alkyl group containing at least one heteroatom selected from oxygen, sulfur or nitrogen containing from 2 to 16 carbon atoms or a branched alkyl group containing at least one heteroatom selected from oxygen, sulfur or nitrogen containing from 3 to 16 carbon atoms, a straight or branched alkyl group of from 2 to 16 carbon atoms and substituted with at least on hydroxyl or amino group, —$NR^5R^6$ where $R^5$ and $R^6$ are independently hydrogen or a straight chain alkyl group of from 1 to 16 carbon atoms, a branched chain alkyl group of from 3 to 16 carbon atoms, an aryl group of from 6 to 10 carbon atoms or an aralkyl group of from 7 to 12 carbon atoms.

7. The process of claim 1 wherein the metal transesterification catalyst is of general formula (III):

$$M^{n+}(X)_n \quad (III)$$

wherein:
M is a metal that is catalytically active for transesterification;
X is $OR^7$, where each $R^7$ is independently a monovalent straight chain alkyl group of from 1 to 12 carbon atoms, a branched chain alkyl group of 3 to 12 carbon atoms, a cycloalkyl group of from 3 to 12 carbon atoms, an aryl group of from 6 to 10 carbon atoms, an aralkyl group of from 9 to 12 carbon atoms, an alkenyl group of 2 to 12 carbon atoms, an acyl group of from 1 to 12 carbon atoms, or two $OR^7$ groups are bonded to each other through a carbon-carbon linkage to form a —O—$R^7$—$R^7$—O— group, or X is $R^8$ where $R^8$ is a monovalent straight chain alkyl group of from 1 to 16 carbon atoms, a branched chain alkyl group of from 3 to 16 carbon atoms, a cycloalkyl group of from 3 to 12 carbon atoms, an aryl group of from 6 to 10 carbon atoms or an aralkyl group of from 7 to 12 carbon atoms, with the proviso that at least one X is $OR^7$; and,
n is the valence of M.

8. The process of claim 1 wherein following removal of the catalyst, the residual level of metal in the alkoxysilane transesterification reaction product is less than about 100 ppm based on the weight of the alkoxysilane transesterification reaction product.

9. The process of claim 1 wherein following removal of the catalyst, the residual level of metal in the alkoxysilane transesterification reaction product is less than about 50 ppm.

10. The process of claim 1 wherein following removal of the catalyst, the residual level of metal in the alkoxysilane transesterification reaction product is less than about 10 ppm.

11. The process of claim 1 further comprising adding an acid to the crude alkoxysilane transesterification reaction product of step (a).

12. The process of claim 11 wherein the acid is acetic acid and/or boric acid.

13. The process of claim 1 further comprising purifying the alkoxysilane transesterification reaction product.

14. A process for preparing an alkoxysilane transesterification reaction product which comprises
(a) transesterifying at least one transesterifiable alkoxysilane with at least one transesterifying alcohol under transesterification reaction conditions in the presence of at least one metal transesterification catalyst accompanied by removal of byproduct and/or unreacted alcohol to produce a crude alkoxysilane transesterification reaction product; and
(b) removing at least part of the metal transesterification catalyst from the reaction product, wherein the metal transesterification catalyst is removed by adding an absorption medium of precipitated silica to the crude alkoxysilane transesterification reaction product of step (a) and stirring the mixture, adsorbing the metal transesterification catalyst on an adsorption medium followed by filtering the adsorption medium containing adsorbed catalyst.

15. The process of claim 14 wherein removing metal transesterification catalyst is carried out by adsorbing metal transesterification catalyst therein on adsorption medium and separating metal transesterification catalyst-containing adsorption medium from the transesterification reaction medium by filtration or decantation to provide a transesterification catalyst-depleted transesterification medium.

16. The process of claim 15 wherein alkoxysilane transesterification reaction product is recovered from the transesterification catalyst-depleted transesterification reaction medium by distillation.

17. A process for preparing an alkoxysilane transesterification reaction product comprising:
(a) adding a metal transesterification catalyst to a transesterifiable alkoxysilane in the amount of from 0.01 weight percent to 5 weight percent, based on the weight of the transesterifiable alkoxysilane, to form a mixture;
(b) heating the mixture from step (a) under conditions sufficient to effect a transesterification reaction;
(c) adding a transesterifying alcohol into the mixture during heating step (b);
(d) removing byproduct alcohol formed during the transesterification reaction;
(e) hydrolyzing the metal transesterification catalyst to form a metal oxide of said catalyst;
(g) removing the metal oxide to form a alkoxysilane transesterification reaction product; and, optionally,
(h) further purifying the alkoxysilane transesterification reaction product of step (g).

18. The process of claim 17 wherein the transesterifiable alkoxysilane is a transesterifiable alkoxysilane of general formula (I):

$$Y—[R^1—Si(R^2)_{3-a}(OR^3)_a]_b \qquad (I)$$

wherein:
Y is hydrogen, halo or a functional group;
each $R^1$ independently is a divalent straight chain alkylene group of from 1 to 12 carbon atoms, a branched chain alkylene of from 2 to 12 carbon atoms, a cycloalkylene group of from 3 to 12 carbon atoms, an arylene group of from 6 to 10 carbon atoms, an aralkyl group of from 7 to 16 carbon atoms, an alkylene group of from 2 to 12 carbon atoms, a cycloalkylene group of from 3 to 12 carbon atoms, an alkynylene group of from 2 to 12 carbon atoms, a straight, branched or cyclic alkylene group containing at least one heteroatom selected from sulfur, oxygen or nitrogen and from 2 to 12 carbon atoms, or a chemical bond, with the proviso that where $R^1$ is a chemical bond, Y is an organofunctional group and the silicon atom is bonded to a carbon atom of the group Y;
each $R^2$ independently is a monovalent straight chain alkyl group containing 1 to 16 carbon atoms, a branched alkyl group containing 3 to 16 carbon atoms, a cycloalkyl group containing 3 to 12 carbon atoms, an aryl group containing 6 to 10 carbon atoms, an aralkyl group containing 7 to 16 carbon atoms;
each $R^3$ independently is a monovalent straight chain alkyl group of from 1 to 4 carbon atoms or a branched chain alkyl group having 3 to 4 carbon atoms;
a is an integer of from 1 to 3; and,
b is an integer of from 1 to 4, the alcohol is of general formula (II):

$$R^4OH \qquad (II)$$

wherein:
$R^4$ is a monovalent straight chain alkyl group of from 1 to 16 carbon atoms, a branched chain alkyl group of from 3 to 16 carbon atoms, a cycloalkyl group of from 3 to 12 carbon atoms, an alkenyl group of from 2 to 16 carbon atoms, an aralkyl group of from 7 to 12 carbon atoms, an aryl group of from 6 to 10 carbon atoms, a straight chain alkyl group containing at least one heteroatom selected from oxygen, sulfur or nitrogen containing from 2 to 16 carbon atoms or a branched alkyl group containing at least one heteroatom selected from oxygen, sulfur or nitrogen containing from 3 to 16 carbon atoms, a straight or branched alkyl group of from 2 to 16 carbon atoms and substituted with at least on hydroxyl or amino group, —$NR^5R^6$ where $R^5$ and $R^6$ are independently hydrogen or a straight chain alkyl group of from 1 to 16 carbon atoms, a branched chain alkyl group of from 3 to 16 carbon atoms, an aryl group of from 6 to 10 carbon atoms or an aralkyl group of from 7 to 12 carbon atoms,
and the metal transesterification catalyst is of general formula (III):

$$M^{n+}(X)_n \qquad (III)$$

wherein:
M is a metal that is catalytically active for transesterification;
X is $OR^7$, where each $R^7$ is independently a monovalent straight chain alkyl group of from 1 to 12 carbon atoms, a branched chain alkyl group of 3 to 12 carbon atoms, a cycloalkyl group of from 3 to 12 carbon atoms, an aryl group of from 6 to 10 carbon atoms, an aralkyl group of from 9 to 12 carbon atoms, an alkenyl group of 2 to 12 carbon atoms, an acyl group of from 1 to 12 carbon atoms, or two $OR^7$ groups are bonded to each other through a carbon-carbon linkage to form a —O—$R^7$—$R^7$—O— group, or X is $R^8$ where $R^8$ is a monovalent straight chain alkyl group of from 1 to 16 carbon atoms, a branched chain alkyl group of from 3 to 16 carbon atoms, a cycloalkyl group of from 3 to 12 carbon atoms, an aryl group of from 6 to 10 carbon atoms or an aralkyl group of from 7 to 12 carbon atoms, with the proviso that at least one X is $OR^7$;
n is the valence of M.

19. The process of claim 17 wherein in step (e), removing metal transesterification catalyst from the transesterification reaction medium is carried out by hydrolyzing metal transesterification catalyst therein to provide metal oxide and separating metal oxide hydrolysate from the transesterification reaction medium by filtration or decantation to provide a transesterification catalyst-depleted transesterification medium.

20. The process of claim 19 wherein alkoxysilane transesterification reaction product is recovered from the transesterification catalyst-depleted transesterification reaction medium by distillation.

* * * * *